US009968743B2

(12) United States Patent
Kuwahara et al.

(10) Patent No.: US 9,968,743 B2
(45) Date of Patent: May 15, 2018

(54) QUANTITATIVE SYRINGE-TYPE EJECTOR

(71) Applicants: Katsuhito Kuwahara, Tokyo (JP); Shinya Hoshino, Tokyo (JP)

(72) Inventors: Katsuhito Kuwahara, Tokyo (JP); Shinya Hoshino, Tokyo (JP)

(73) Assignee: YOSHINO KOGYOSHO CO., LTD., Tokyo (JP)

( * ) Notice: Subject to any disclaimer, the term of this patent is extended or adjusted under 35 U.S.C. 154(b) by 444 days.

(21) Appl. No.: 14/443,144

(22) PCT Filed: Nov. 27, 2013

(86) PCT No.: PCT/JP2013/006980
§ 371 (c)(1),
(2) Date: May 15, 2015

(87) PCT Pub. No.: WO2014/083849
PCT Pub. Date: Jun. 5, 2014

(65) Prior Publication Data
US 2015/0328409 A1    Nov. 19, 2015

(30) Foreign Application Priority Data

Nov. 30, 2012   (JP) .................................. 2012-263572
Jun. 28, 2013   (JP) .................................. 2013-137432

(51) Int. Cl.
*A61M 5/315*   (2006.01)
*A61M 11/00*   (2006.01)
(Continued)

(52) U.S. Cl.
CPC .... *A61M 5/31501* (2013.01); *A61M 5/31526* (2013.01); *A61M 5/31573* (2013.01);
(Continued)

(58) Field of Classification Search
CPC ............ A61M 5/19; A61M 2005/1787; A61M 5/2448; A61M 5/284; A61M 5/31596;
(Continued)

(56) References Cited

U.S. PATENT DOCUMENTS 5,688,250 A * 11/1997 Naganuma ............... A61M 5/24
604/200
6,796,969 B1 * 9/2004 Andersson ............ A61M 5/322
604/110
(Continued)

FOREIGN PATENT DOCUMENTS

JP    H07-213612 A    8/1995
JP    2012-110732 A   6/2012
(Continued)

OTHER PUBLICATIONS

Feb. 18, 2014 International Search Report issued in International Application No. PCT/JP2013/006980.
(Continued)

*Primary Examiner* — Bhisma Mehta
*Assistant Examiner* — James D Ponton
(74) *Attorney, Agent, or Firm* — Oliff PLC

(57) ABSTRACT

A quantitative syringe-type ejector capable of ejecting the contents packed in one syringe in small quantities is provided. The quantitative syringe-type ejector includes a syringe and a plunger. The plunger includes a piston holding member and a plunger operation member. The piston holding member has at least one arm having: a slide projection slidable on an inner peripheral surface of the syringe; and a lock projection to be releasably locked to a back end of the syringe. The plunger operation member has a lock part to be releasably locked to the back end of the syringe.

12 Claims, 17 Drawing Sheets

(51) Int. Cl.
    *A61M 15/08*    (2006.01)
    *B05B 11/00*    (2006.01)
    *A61M 5/31*    (2006.01)

(52) U.S. Cl.
    CPC ...... *A61M 5/31578* (2013.01); *A61M 11/007* (2014.02); *A61M 15/08* (2013.01); *B05B 11/00* (2013.01); *A61M 2005/3139* (2013.01)

(58) Field of Classification Search
    CPC .... A61M 11/007; A61M 11/08; A61M 5/315; A61M 5/31501; A61M 5/31505; A61M 5/31526; A61M 5/3153; A61M 5/31536; A61M 5/31595; A61M 2005/31506; A61M 2005/31508; A61M 15/0028; A61M 15/009; A61M 15/08; B05B 11/025
    See application file for complete search history.

(56) References Cited

U.S. PATENT DOCUMENTS 7,967,010 B2 * 6/2011 Vedrine ............... A61M 5/2429
                                                    128/200.14
9,017,287 B2 * 4/2015 Bicknell ............ A61M 5/2033
                                                    604/135
2010/0145275 A1    6/2010 Grunhut et al.
2016/0175541 A1 * 6/2016 Thorley ............. A61M 5/3234
                                                    604/110

FOREIGN PATENT DOCUMENTS

WO    99/55402 A1    11/1999
WO    2011/111006 A2    9/2011
WO    2012/002398 A1    1/2012
WO    2012/157582 A1    11/2012
WO    2013/145789 A1    10/2013

OTHER PUBLICATIONS

Jun. 1, 2016 Extended Search Report issued in European Patent Application No. 13859567.3.

Sep. 1, 2016 Office Action issued in Chinese Patent Application No. 201380061859.7.

* cited by examiner

QUANTITATIVE SYRINGE-TYPE EJECTOR

TECHNICAL FIELD

The disclosure relates to a quantitative syringe-type ejector including a syringe and a plunger pushable into the syringe.

BACKGROUND

In syringe-type ejectors, for example, a piston (gasket) having a plunger rod (plunger) is placed in a syringe to form a packing space for contents (e.g. a chemical solution) between the syringe and the piston, and the contents in the packing space are ejected outside by pushing the plunger rod (for example, see Patent Literature (PTL) 1).

CITATION LIST

Patent Literature

PTL 1: JP H7-213612 A

In conventional syringe-type ejectors, however, the piston is pushed inside the syringe at once without being regulated, and accordingly it is difficult to eject the contents packed in one syringe in small quantities.

It could be helpful to provide a new quantitative syringe-type ejector capable of ejecting the contents packed in one syringe in small quantities.

SUMMARY

The quantitative syringe-type ejector includes: a syringe; and a plunger pushable into the syringe, wherein the plunger includes: a piston holding member having a piston in front and at least one arm extending backward; and a plunger operation member located behind the piston holding member to press the arm forward, the piston holding member has, on the arm: a slide projection for deforming the arm inward while sliding on an inner peripheral surface of the syringe; and a lock projection located behind the slide projection to be locked to a back end of the syringe, the lock of the lock projection to the back end of the syringe is released when the plunger operation member is pushed in a state where the arm is deformed inward, and the plunger operation member has a lock part to be releasably locked to the back end of the syringe.

The lock projection may be located behind the lock part.

A plurality of the lock parts may be arranged at an interval in an axial direction, and at least one of the plurality of lock parts may be located ahead of the lock projection.

The lock projection may be locked so that the lock to the back end of the syringe is released when pressed by the plunger operation member.

A level difference for being pressed by the plunger operation member may be provided on an inner side of a back end of the arm. A side surface of the level difference may be a tapered surface.

The plunger operation member may have a projection on an inner side of a pressing part for pressing the arm.

The plunger operation member may have a notch for operably housing the arm, and an abutting end provided on the plunger operation member defining the notch may be a pressing part for pressing the arm.

The abutting end of the plunger operation member may have a tapered surface.

The quantitative syringe-type ejector may include a slip-off prevention part for holding the piston holding member and the plunger operation member so as not to slip off, while enabling the plunger operation member to be pushed back.

The lock part may be a protuberance protruding from the plunger operation member.

The lock part may be an elastically deformable reverse part projecting from the plunger operation member.

A spray nozzle may be provided at a front end of the syringe.

Upon pushing the plunger, the user is required to apply a force that causes the lock part of the plunger operation member to climb over the back end of the syringe and, when the lock between the lock part and the back end of the syringe is released, is allowed to push the plunger forcefully.

Moreover, by relaxing or releasing the push of the plunger operation member and then pushing the plunger operation member forcefully again, the second ejection can be performed. The contents can be pushed out forcefully in this way. Thus, the contents packed in one syringe can be stably ejected in small quantities while maintaining a constant state. Besides, the user does not need to switch the ejector from one hand to the other upon the second ejection. The user can therefore expel the contents in small quantities with one hand.

DETAILED DESCRIPTION

The following describes the disclosed quantitative syringe-type ejector in detail using various embodiments below, with reference to drawings.

Figure 1:
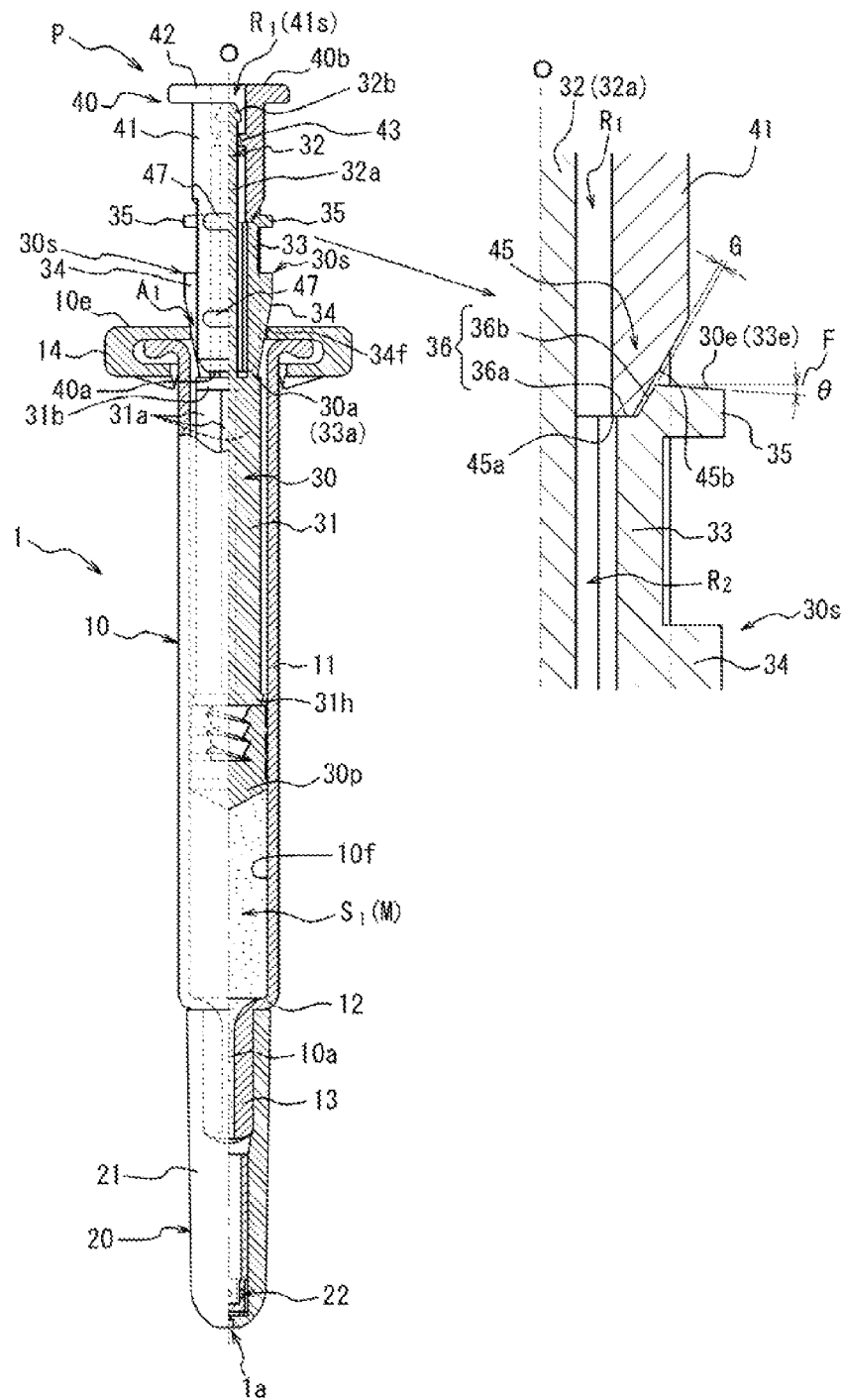
FIG. 1 is a side view illustrating a partial section of a collunarium ejector which is a first embodiment of the disclosed quantitative syringe-type ejector in an initial state before pushing a plunger operation member, and a partially enlarged view thereof.

In an overall view in FIG. 1, reference sign 1 is a collunarium ejector which is a first embodiment of the disclosed quantitative syringe-type ejector. The collunarium ejector 1 includes a syringe 10 made of a synthetic resin or glass. The syringe 10 has a hollow barrel 11 that can be filled with contents (e.g. collunarium in this embodiment) M, with a front end 13 being integrally connected to the barrel 11 via a shoulder 12. The front end 13 is smaller in diameter than the barrel 11. A through hole 10a is formed inside the front end 13.

Reference sign 20 is a nozzle removable from the syringe 10. The nozzle 20 has a body 21 removably fitted with the front end 13 of the syringe 10. The body 21 contains a nozzle tip 22. The body 21 also has, at its front end, an ejection opening 1a into the nozzle tip 22. Thus, the contents M can be sprayed from the nozzle 20 to the outside through the ejection opening 1a.

A finger holder 14 projecting outward is separately provided at the back end of the barrel 11 of the syringe 10. An opening (hereafter "back end opening") $A_1$ from inside the syringe 10 to the outside is formed in the finger holder 14. The back end of the finger holder 14 constitutes a back end 10e of the syringe 10. The finger holder 14 may be formed integrally with the barrel 11.

Reference sign P is a plunger made of a synthetic resin and housed in the syringe 10. The plunger P includes a piston holding member 30 and a plunger operation member 40 located behind the piston holding member 30.

The piston holding member 30 has a body 31 for holding a piston 30p (gasket). The piston 30p is provided at the front end of the body 31. The body 31 integrally includes a fixing part 31h for fixing the piston 30p, vertically long four plate parts 31a combined to form a cross in cross section, and a disc part 31b. The piston 30p is, for example, made of an elastic material such as rubber, and is held slidably on an inner peripheral surface 10f of the syringe 10.

A packing space $S_1$ for packing the contents M is formed between the piston 30p provided in the body 31 and the syringe 10. When the piston 30p is pushed, the contents M are transferred to the through hole 10a formed at the front end 13 of the syringe 10.

Figure 5:
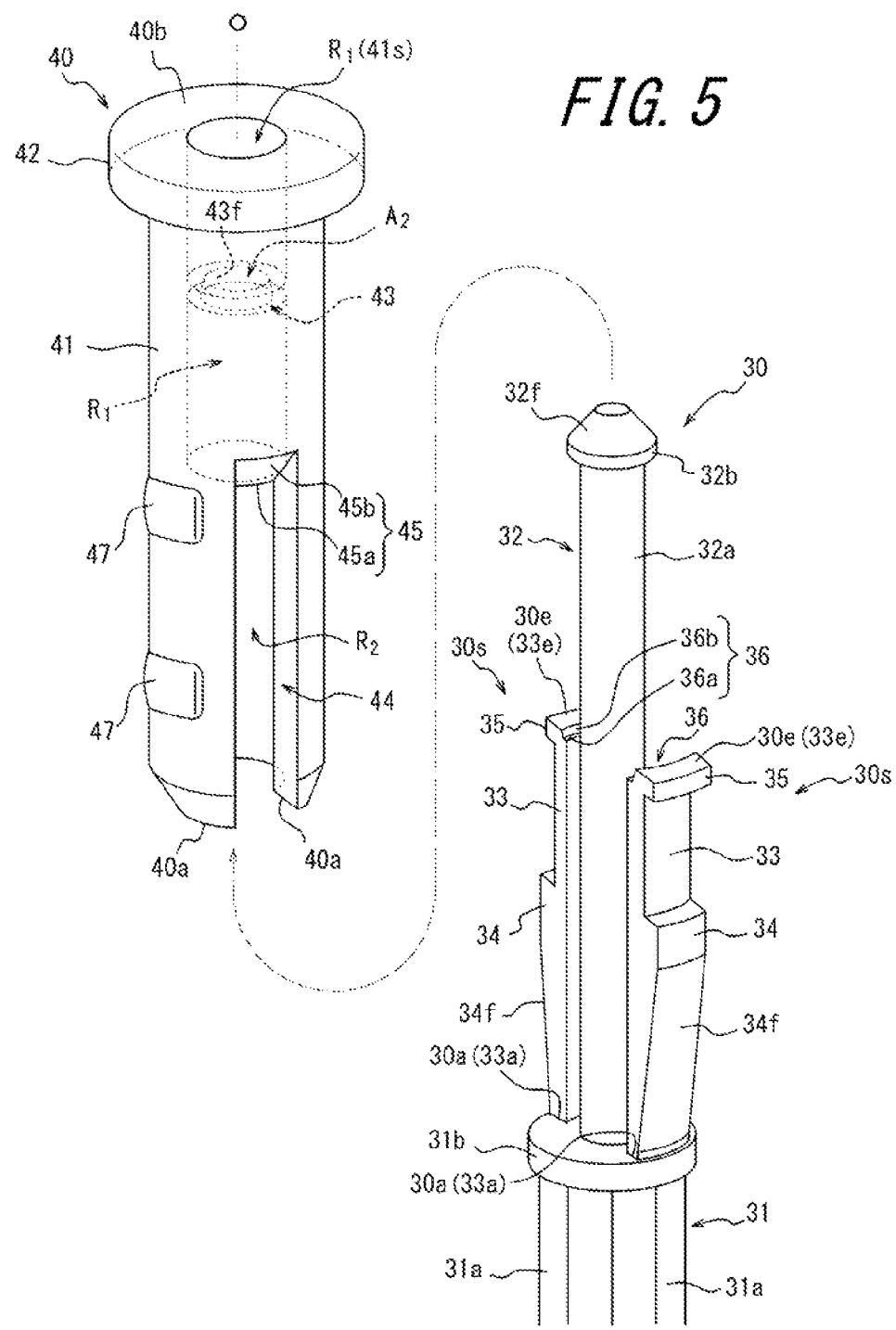
FIG. 5 is an exploded perspective view schematically illustrating a part of a piston holding member and the plunger operation member which are chief components of a plunger according to the first embodiment.

The body 31 is also integrally provided with a shaft 32. The shaft 32 extends backward from the disc part 31b along an axis O (the center axis of the collunarium ejector 1). As illustrated in FIG. 5, the shaft 32 has a shaft body 32a that is connected to the disc part 31b and is smaller in diameter than the disc part 31b. A head 32b larger in diameter than the shaft body 32a is integrally provided at the tip (back end) of the shaft body 32a. The head 32b has an inclined surface 32f to taper backward.

The body 31 of the piston holding member 30 is also integrally provided with two stoppers 30s. The stoppers 30s face each other with the shaft 32 in between. The stoppers 30s are made up of arms 33 that are integrally fixed to the disc part 31b. Each arm 33 is shaped like a flat plate, and extends backward along the axis O from its fixed end 33a fixed to the disc part 31b. From the initial position illustrated in FIG. 1 (the position in the overall view in FIG. 1), each arm 33 can be deformed inward in the radial direction (the direction orthogonal to the axis O) with the fixed end 33a as the origin, by applying an external force. Each arm 33 can be restored to the initial position by releasing the load such as the external force. Thus, the fixed ends 33a of the arms 33 function as fixed ends 30a of the stoppers 30s. In other words, each stopper 30s can be deformed with the fixed end 30a as the origin by applying the external force from the initial position, and restored to the initial position with the fixed end 30a as the origin by releasing the load such as the external force. In this embodiment, each arm 33 is formed thin so as to be easily deformed and restored.

Each stopper 30s has one slide projection 34 provided integrally with the arm 33. The slide projections 34 project so as to face the inner peripheral surface 10f of the syringe 10, and are located on opposite sides of the axis O, as illustrated in the overall view in FIG. 1. The distance between the maximum outer diameters of the two slide projections 34 in the radial direction is greater than the inner diameter (equal to or less than the inner diameter of the syringe 10 in this embodiment) of the back end opening $A_1$ of the syringe 10, as illustrated in the overall view in FIG. 1. Upon contact with the back end 10e of the syringe 10, the slide projections 34 are allowed to enter into the syringe 10 and slide on the inner peripheral surface 10f of the syringe 10 as a result of the arms 33 being flexure-deformed with the fixed ends 33a as the origin.

In this embodiment, each slide projection 34 has an inclined surface 34f to taper toward the fixed end 33a of the arm 33 (the fixed end 30a of the stopper 30s). This eases the entrance of the slide projection 34 into the syringe 10 from the back end opening $A_1$ of the syringe 10.

Each stopper 30s also has a lock projection 35 provided integrally with the arm 33. The lock projection 35 projects outward in the radial direction. The lock projection 35 is located behind the slide projection 34, with a gap therebetween. The distance between the maximum outer diameters of the two lock projections 35 in the radial direction is greater than the inner diameter of the back end opening $A_1$ of the syringe 10, as illustrated in the overall view in FIG. 1. Thus, upon contact with the back end 10e of the syringe 10, the lock projections 35 are caught by the back end 10e of the syringe 10 and locked. The lock projections 35 thus function as a stopper for restricting the entrance of the piston holding member 30 into the syringe 10.

In this embodiment, a free end 33e of each arm 33 is tapered forward at an angle θ with respect to a plane (horizontal plane) F orthogonal to the axis O toward the outer side in the radial direction, as illustrated in the enlarged view in FIG. 1. For example, the angle θ is set so that the free end 33e of the arm 33 is in parallel with the horizontal line F when the arm 33 is inclined diagonally inward (the direction in which the arm 33 is inclined to be closer to the axis O toward the back) with the fixed end 33a as the origin. In this embodiment, each lock projection 35 is formed integrally at the free end 33e of the arm 33. The back ends of the lock projections 35 thus constitute the free ends 33e of the arms 33. In other words, in this embodiment, the back ends of the lock projections 35 function as free ends 30e of the stoppers 30s. Note that the value of θ may be changed as appropriate depending on the size of the collunarium ejector and the like.

In addition, in this embodiment, a level difference 36 is provided in each lock projection 35, as illustrated in the enlarged view in FIG. 1. The level difference 36 is formed in the inner surface of the stopper 30s. In this embodiment, the level difference 36 is formed as a pressed part by notching the inner side of the free end 33e of the arm 33, as illustrated in the enlarged view in FIG. 1. The level difference 36 is formed by a flat level difference bottom surface 36a and a level difference side surface 36b leading to the level difference bottom surface 36a. In this embodiment, the level difference side surface 36b is a tapered surface that is inclined outward in the radial direction from the level difference bottom surface 36a toward the free end 33e of the arm 33.

The plunger operation member 40 has a body 41, as illustrated in the overall view in FIG. 1. The plunger operation part 42 for pushing the piston holding member 30 by the user is provided integrally at the back end of the body 41. The body 41 has a cylindrical shape, as illustrated in FIG. 5. Internal spaces $R_1$ and $R_2$ cut through the plunger operation member 40 are formed from a front end 40a to back end 40b of the plunger operation member 40. The shaft 32 of the piston holding member 30 slidably passes through the internal spaces $R_1$ and $R_2$. In this embodiment, the shaft 32 is placed in the internal space $R_1$ to restrict the movement (wobbling) of the plunger operation member 40 around the axis O.

An annular projection 43 is provided on the inner peripheral surface of the plunger operation member 40 defining the internal space $R_1$, as illustrated in FIG. 5. The annular projection 43 projects from the inner side of the body 41, with its inner edges forming an opening $A_2$ smaller in diameter than the internal space $R_1$. The opening $A_2$ forms an inner diameter that is larger than the outer diameter of the shaft body 32a of the piston holding member 30 and smaller than the head 32b. The annular projection 43 has the shaft body 32a of the piston holding member 30 pass through, and holds the head 32b so as not to slip off, as illustrated in the overall view in FIG. 1. The head 32b and the annular projection 43 thus function as a slip-off prevention part for holding the piston holding member 30 and the plunger operation member 40 so as not to slip off.

In particular, in this embodiment, the inner peripheral surface 43f of the annular projection 43 is tapered backward as illustrated in FIG. 5. This allows the head 32b to be easily attached to the upper end of the annular projection 43 through the opening $A_2$. Moreover, the annular projection 43, by being provided in the internal space $R_1$, forms a clearance space 41s. With the head 32b being housed in the internal space $R_1$ closer to the back end than the annular projection 43, the clearance space 41s allows the piston holding member 30 and the plunger operation member 40 to move forward and backward relative to each other along the axis O. In this way, while the piston holding member 30 and the plunger operation member 40 are connected to form the plunger P, the piston holding member 30 and the plunger operation member 40 can be moved relative to each other along the axis O within the range of the clearance formed in the direction of the axis O between the head 32b and the annular projection 43.

The body 41 of the plunger operation member 40 has a plurality of notches 44 into the internal space $R_2$ larger in inner diameter than the internal space $R_1$, as illustrated in FIG. 5. Each notch 44 extends backward from the front end 40a of the plunger operation member 40 to the internal space $R_1$. In this embodiment, two notches 44 are formed to face each other with the axis O in between, in correspondence with the stoppers 30s. Each notch 44 has a width slightly greater than the horizontal width of the arm 33 as illustrated in FIG. 2, and ensures the movement of the stopper 30s along the radial direction by operably containing the arm 33.

Figure 2:
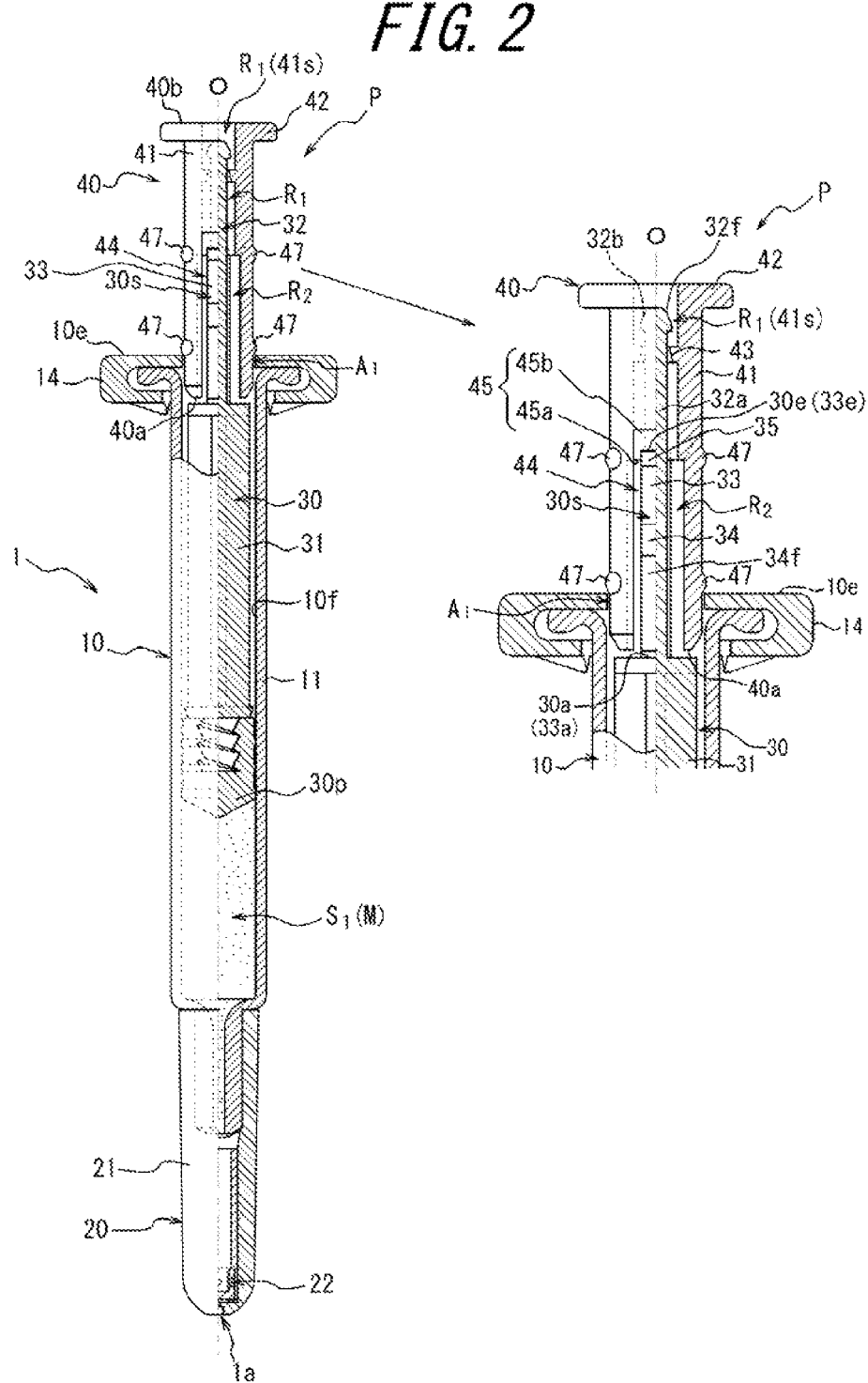
FIG. 2 is another side view illustrating a partial section of the collunarium ejector in the initial state illustrated in FIG. 1, and a partially enlarged view thereof.

The body 41 of the plunger operation member 40 is also provided with an abutting end 45 onto which the arm 33 housed in the notch 44 abuts, as illustrated in the enlarged view in FIG. 2. The abutting end 45 is formed as a pressing part for pressing the arm 33. The abutting end 45, by coming into contact with the back end 33e of the arm 33, can restrain the stopper 30s between the piston 30p and the plunger operation member 40. In this embodiment, the abutting end 45 is formed by an abutting end surface 45a and an abutting side surface 45b leading to the abutting end surface 45a, as illustrated in the enlarged view in FIG. 1. In this embodiment, the abutting end surface 45a is a flat surface, as illustrated in the enlarged view in FIG. 1. The abutting end surface 45a functions as a pressing surface for pressing the level difference bottom surface 36a which is provided on the arm 33 of the piston holding member 30 as a pressed surface. In detail, when the plunger operation member 40 is pushed, the abutting end surface 45a provided on the plunger operation member 40 presses the level difference bottom surface 36a of the piston holding member 30. Thus, by pushing the plunger operation member 40, the piston holding member 30 can be pushed into the syringe 10.

The abutting side surface 45b is a tapered surface that is inclined outward in the radial direction toward the back from the abutting end surface 45a. In this embodiment, the inclination angle of the abutting side surface 45b is substantially equal to that of the level difference side surface 36b of the piston holding member 30. Moreover, in this embodiment, when the level difference bottom surface 36a of the piston holding member 30 and the abutting end surface 45a of the plunger operation member 40 are brought into contact with each other, there is a gap G between the level difference side surface 36b of the piston holding member 30 and the abutting side surface 45b of the plunger operation member 40. Note that the gap G need not necessarily be provided.

The body 41 of the plunger operation member 40 is also provided integrally with a plurality of lock parts 47 on opposite sides of the axis O, as illustrated in FIG. 2. The lock parts 47 are provided at two positions between the notches 44 in the circumferential direction, and also provided on the front end 40a side of the plunger operation member 40. Each lock part 47 is a protuberance that protrudes integrally from the plunger operation member 40. The maximum outer diameter between the two lock parts 47 facing each other in the radial direction is larger than the inner diameter of the back end opening $A_1$ of the syringe 10, as illustrated in FIG. 2. The lock parts 47 are accordingly caught by the back end 10e of the syringe 10 to be locked to the syringe 10.

In this embodiment, the lock between the lock parts 47 of the plunger operation member 40 and the back end 10e of the syringe 10 can be released when the lock parts 47 press the back end 10e of the syringe 10 with at least a predetermined force. In this embodiment, the difference (the amount of contact with the back end 10e of the syringe 10) between the maximum outer diameter between the two lock parts 47 facing each other in the radial direction and the inner diameter of the back end opening $A_1$ of the syringe 10 is adjusted to enable the lock to be released with the predetermined force. In detail, the maximum outer diameter between the two lock parts 47 facing each other in the radial direction and the inner diameter of the back end opening $A_1$ of the syringe 10 are set so that, when the plunger P is pushed to press the lock parts 47 against the back end 10e of the syringe 10 with at least the predetermined force, the lock parts 47 climb over the back end 10e of the syringe 10. Thus, the lock parts 47 are locked to the back end 10e of the syringe 10 in a state of being able to climb over the back end 10e. The predetermined force necessary to release the lock may be set as appropriate depending on the user, the contents, the purpose of use, etc.

The lock parts 47 are arranged at an interval in the direction of the axis O, as illustrated in FIG. 2. In this embodiment, the lock parts 47 are arranged at two positions with an interval in the direction of the axis O, in each of the portions of the body 41 separated by the notches 44. In more detail, one lock part 47 (first lock part) is provided at the same position in the direction of the axis O as the inclined surface 34f of the slide projection 34, and one lock part 47 (second lock part) is provided at the same position in the direction of the axis O as the lock projection 35, as illustrated in the enlarged view in FIG. 2. In this embodiment, each lock part 47 projects from the body 41 in the shape of a dome in a longitudinal section. Moreover, the lock parts 47 are shaped like a track in outline (two semicircles with pairs of their corresponding ends being each connected by one straight line), as illustrated in the overall view in FIG. 1. Note that the outline of the lock parts 47 as seen from the outer surface of the body 41 is not limited to a track, and may be any of various shapes such as an ellipse whose major axis extends along the width direction (circumferential direction) of the body 41.

The method of use in this embodiment is described below.

First, in the state illustrated in FIG. 1, the user has the index finger and the middle finger on the finger holder 14 and places the thumb on the back end 40b of the plunger operation member 40, to hold the collunarium ejector 1. After inserting the nozzle 20 of the collunarium ejector 1 into one nostril, the user pushes the plunger operation member 40. In this embodiment, the user needs to push the plunger operation member 40 until the lock between the lock parts 47 of the plunger operation member 40 and the back end 10e of the syringe 10 is released. In other words, the user needs to apply a force that causes the lock parts 47 of the plunger operation member 40 to climb over the back end 10e of the syringe 10, and the lock parts 47 do not climb over the back end 10e of the syringe 10 until the applied force reaches the predetermined force. Thus, the plunger operation member 40 cannot be pushed together with the piston holding member 30 until the force of pushing the plunger operation member 40 reaches the predetermined force or more. When the user further presses the plunger operation member 40, the force reaches the predetermined force and the lock parts 47 climb over the back end 10e of the syringe 10, thus releasing the lock between the lock parts 47 and the back end 10e of the syringe 10. Hence, pushing the plunger operation member 40 with a stronger force releases the lock between the lock parts 47 of the plunger operation member 40 and the back end 10e of the syringe 10, as a result of which the plunger operation member 40 can be pushed swiftly with a lot of force.

Figure 3A:
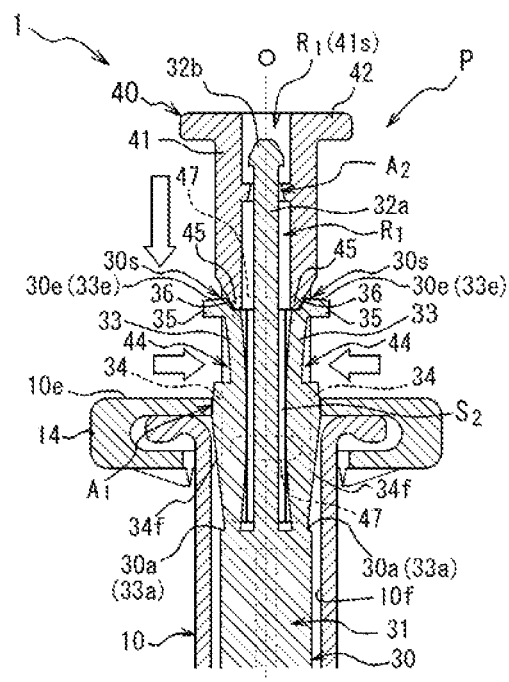
FIG. 3A is an enlarged sectional view illustrating the collunarium ejector in a state when the plunger operation member has been pushed to start the first ejection according to the first embodiment.

When the plunger operation member 40 is pushed, the abutting end surface 45a of the plunger operation member 40 presses the level difference bottom surface 36a of the piston holding member 30, as illustrated in the enlarged view in FIG. 1. As a result, the piston holding member 30, together with the plunger operation member 40, is pushed into the syringe 10 as the plunger P. In this embodiment, the slide projection 34 of the arm 33 has the inclined surface 34f. Accordingly, the slide projection 34 can easily enter into the syringe 10 from the back end opening $A_1$ of the syringe 10, as illustrated in FIG. 3A. Here, the abutting end surface 45a of the plunger operation member 40 presses the level difference bottom surface 36a of the piston operation member 30 with a lot of force. With this swift and strong force received from the plunger operation member 40, the slide projection 34 of the arm 33 enters from the back end opening $A_1$ of the syringe 10 and slides along the inner peripheral surface 10f of the syringe 10 without stopping. Thus, when the force of pressing the plunger operation member 40 reaches the predetermined force, the piston holding member 30 in the syringe 10 can be pushed swiftly with a strong force. At this moment, the piston holding member 30 forcefully and swiftly pushes out the contents M in the syringe 10 from the through hole 10a of the syringe 10. As a result of being forcefully and swiftly pushed out from the through hole 10a of the syringe 10, the contents M can be stably ejected from the ejection opening 1a formed in the nozzle 20 while maintaining a constant state.

Here, pushing the piston holding member 30 is realized by the abutting end surface 45a of the plunger operation member 40 coming into contact with the level difference bottom surface 36a of the arm 33 provided in the piston holding member 30, as illustrated in the enlarged view in FIG. 1. The piston holding member 30 is slidably held in the syringe 10 via the piston 30p. Since the abutting end surface 45a of the plunger operation member 40 and the level difference bottom surface 36a of the arm 33 provided in the piston holding member 30 are kept in contact with each other and the abutting end 45 of the plunger operation member 40 is housed in the level difference 36 of the arm 33, the level difference side surface 36b of the arm 33 functions as a regulation part for regulating the inward displacement of the arm 33.

Figure 3B:
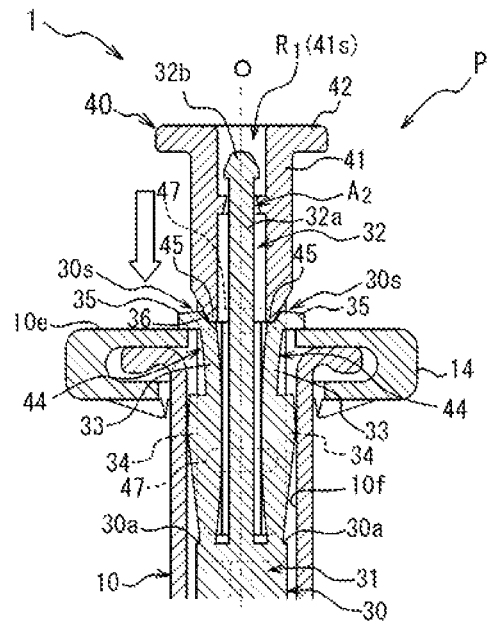
FIG. 3B is an enlarged sectional view illustrating the collunarium ejector in a state when the first ejection illustrated in FIG. 3A has ended.

In detail, in this embodiment, when the piston holding member 30 is pushed into the syringe 10, for example, the slide projection 34 of the arm 33 comes into contact with the back end opening $A_1$ of the syringe 10, as illustrated in FIG. 3A. During this, the movement of the free end 33e side of the arm 33 inward in the radial direction is restrained by the abutting end 45. This being so, when the slide projection 34 of the arm 33 enters from the back end opening $A_1$, the radial movement of the fixed end 33a and free end 33e of the arm 33 in the syringe 10 is restrained, so that the arm 33 as a whole is flexure-deformed with the slide projection 34 as the origin, as illustrated in FIG. 3A. While the arm 33 provided in the piston holding member 30 is flexure-deformed between the fixed end 33a and free end 33e of the arm 33 with the slide projection 34 as the origin as illustrated in FIG. 3A, the slide projection 34 slides along the inner peripheral surface 10f of the syringe 10, thus allowing the plunger operation member 40 to be pushed. Therefore, the piston holding member 30 can be pushed along the inner peripheral surface 10f of the syringe 10, where the slide projection 34 forms no obstacle because the arm 33 is flexure-deformed. As a result, the collunarium ejector 1 can eject the contents M in fixed amount from the ejection opening 1a into the nostril until each lock projection 35 provided on the arm 33 comes into contact with the back end 10e of the syringe 10 as illustrated in FIG. 3B.

When each lock projection 35 comes into contact with the back end 10e of the syringe 10, the piston holding member 30 can no longer be pushed, and so the first ejection ends with the contents M being left in the packing space $S_1$. The content of the packing space $S_1$ at this point may be selected as appropriate depending on the purpose of use. For example, the content is half the volume of the packing space $S_1$ before the ejection starts.

Figure 3C:
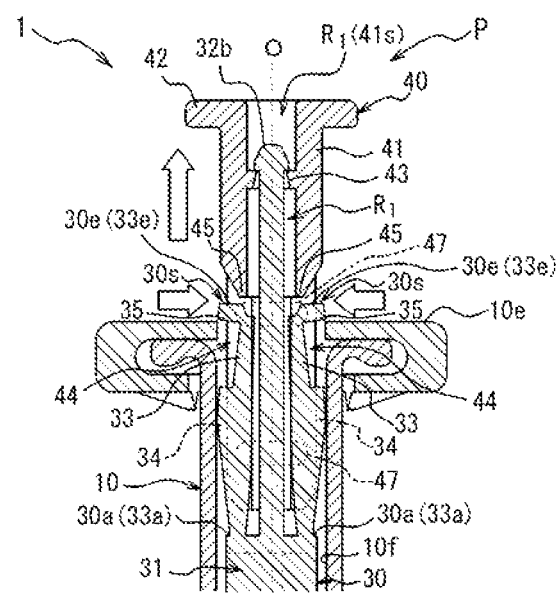
FIG. 3C is an enlarged sectional view illustrating the collunarium ejector in a state when, after the end state illustrated in FIG. 3B, the push of the plunger operation member has been relaxed or released to start the second ejection.

After this, when the push of the plunger operation member 40 is relaxed or released, with the force of restoration from the above-mentioned flexure deformation, the free end 33e side of the arm 33 is restored with the slide projection 34 as the origin, as illustrated in FIG. 3C. Here, since the fixed end 33a side of the arm 33 remains deformed inward with the slide projection 34 as the origin, the free end 33e side of the arm 33 is restored diagonally inward so as to be aligned with the fixed end 33a side which remains deformed inward with the slide projection 34 as the origin, as illustrated in FIG. 3C. The lock projection 35 of the arm 33 is also displaced diagonally inward so as to follow the free end 33e side of the arm 33, as a result of which the state of locking with the lock projection 35 is released as illustrated in FIG. 3C.

Particularly, in this embodiment, when the plunger operation member 40 is pushed, the abutting side surface 45b is regulated by the level difference side surface 36b of the piston holding member 30 and so the piston holding member 30 can be effectively pushed in a state where the deformation of the free end 33e side of the arm 33 is regulated, as described with reference to the enlarged view in FIG. 1. Moreover, when the push of the plunger operation member 40 is released in a state where the arm 33 is flexure-deformed (a state where the lock projections 35 are locked to the back end 10e of the syringe), the arm 33 is restored from the deformation and as a result the abutting side surface 45b is guided along the level difference side surface 36b of the piston holding member 30. Hence, the free end 33e side of the arm 33 escapes from the plunger operation member 40 while easily pushing the plunger operation member 40 back, so that the free end 33e of the arm 33 is deformed inward in the radial direction. The state of locking between the lock projections 35 and the back end 10e of the syringe can be released in this way.

Figure 4:
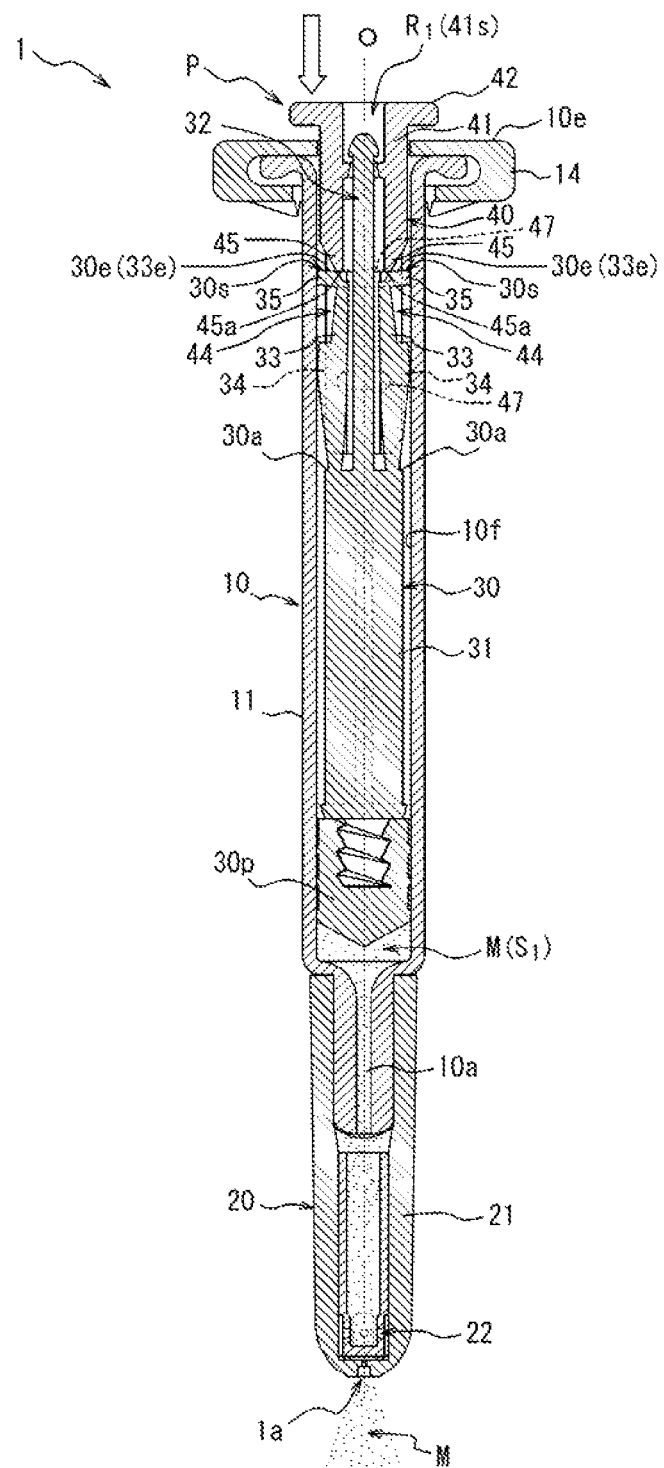
FIG. 4 is a sectional view illustrating the collunarium ejector in a state when the second ejection has been performed according to the first embodiment.

Therefore, by relaxing or releasing the push of the plunger operation member 40 and then pushing the plunger operation member 40 again, the second ejection can be performed. In this embodiment, the lock parts 47 provided at the same position in the axial direction as the lock projections 35 are locked to the back end 10e of the syringe 10 even in a state where the lock between the lock projections 35 and the back end 10e of the syringe has been released, as illustrated in FIG. 3C. Therefore, when pushing again the plunger operation member 40 which has been pushed back, the plunger operation member 40 needs to be pressed with a force that causes the lock parts 47 to climb over the back end 10e of the syringe 10. Upon the second ejection, accordingly, the plunger operation member 40 is pressed with a strong force as in the first ejection operation. This releases the lock between the second lock parts 47 and the back end 10e of the syringe 10, and enables the plunger operation member 40 to be pushed without stopping. As a result, the abutting ends 45 of the plunger operation member 40 can be swiftly pushed against the lock projections 35 (the free ends 33e of the arms 33 or the free ends 30e of the stoppers 30s) of the piston holding member 30 with a lot of force, as illustrated in FIG. 4. It is thus possible to restore the arms 33 with the slide projections 34 as the origin as illustrated in FIG. 3C, and then swiftly push the piston holding member 30 with a lot of force as illustrated in FIG. 4.

In particular, in this embodiment, the free end 33e of each arm 33 provided on the piston holding member 30 is tapered at the angle θ. Accordingly, even when the free end 33e side of the arm 33 is restored with the slide projection 34 as the origin, the contact with the abutting end surface 45a of the plunger operation member 40 can be made in a nearly parallel state as illustrated in FIG. 4, which allows the piston holding member 30 to be pushed smoothly. Note that the free end 33e of the arm 33 may form a flat surface in parallel with the horizontal plane F in the initial state illustrated in the enlarged view in FIG. 1.

Thus, after the push of the plunger operation member 40 is relaxed or released so that the plunger operation member 40 is pushed back as illustrated in FIG. 3C, the nozzle 20 is inserted into the other nostril and the plunger operation member 40 is pushed, as a result of which the contents M remaining in the packing space $S_1$ can be stably ejected from the ejection opening 1a while maintaining a constant state as in the first ejection, as illustrated in FIG. 4.

As described above, according to this embodiment, the contents M packed in one syringe 10 can be stably extracted in small quantities while maintaining a constant spray state. Moreover, in this embodiment, relaxing or releasing the push of the plunger operation member 40 enables the second ejection. The user does not need to switch the collunarium ejector 1 from one hand to the other upon the second ejection. The user can therefore expel the contents in small quantities with one hand.

In this embodiment, since the notches 44 for operably housing the stoppers 30s are formed in the plunger operation member 40, the total length of the plunger P can be reduced, and also wobbling (e.g. the movement of the shaft 32 around the axis O) caused by assembling the piston holding member 30 and the plunger operation member 40 together can be lessened. Thus, according to this embodiment, the contents can be ejected in small quantities while maintaining favorable operation.

Figure 6:
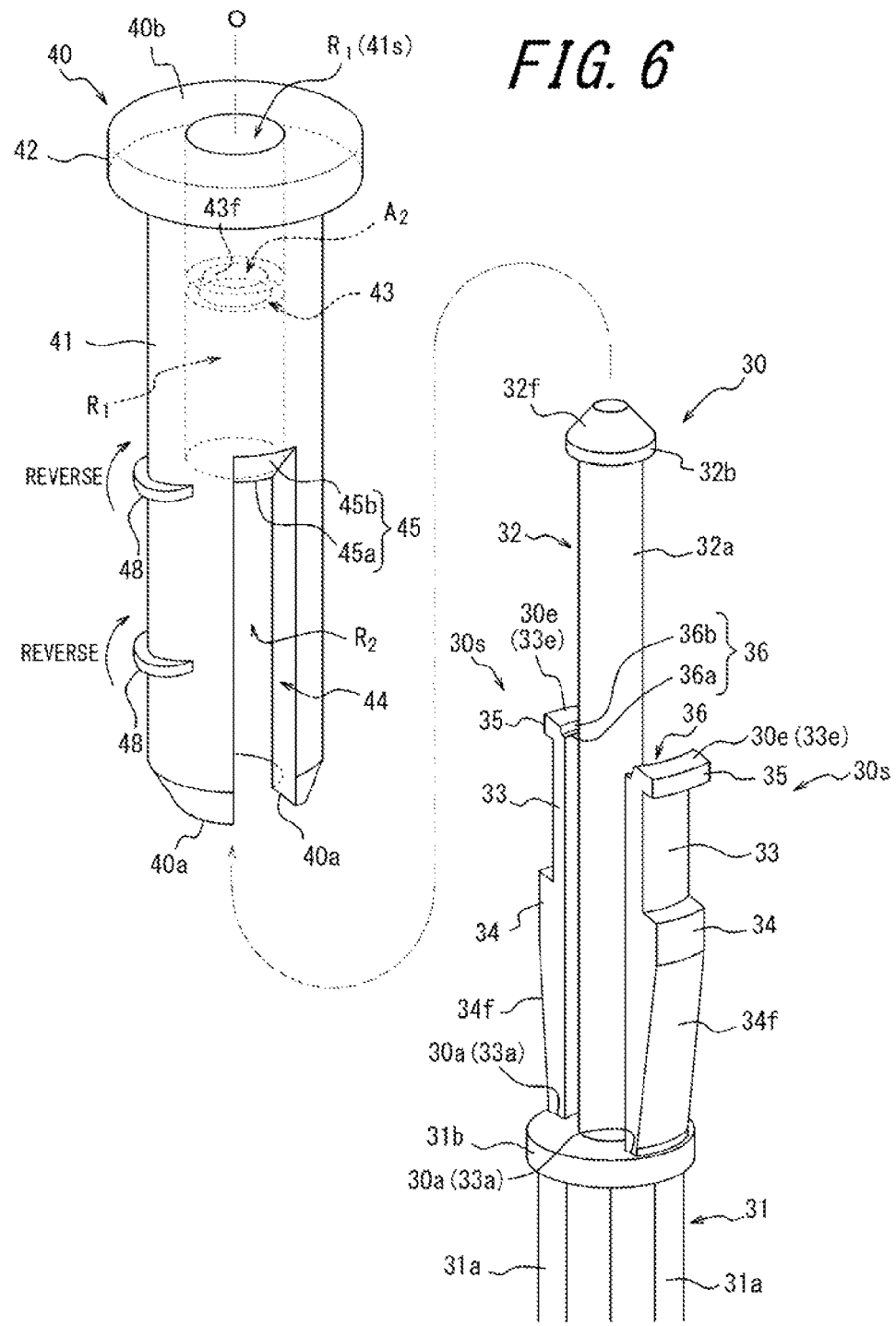
FIG. 6 is an exploded perspective view schematically illustrating a part of a piston holding member and a plunger operation member which are chief components of a plunger in a collunarium ejector which is a second embodiment of the disclosed quantitative syringe-type ejector.

Note that the shape of the lock parts 47 may be changed. FIG. 6 illustrates a modification of the lock parts as a second embodiment. Lock parts 48 according to this embodiment are reverse parts integrally projecting from the plunger operation member 40 and capable of reversing back. The lock parts 48 are formed as elastically deformable blade pieces projecting outward from the body 41 of the plunger operation part 40. The lock parts 48 are inclined toward the front end of the plunger operation member 40. Alternatively, the lock parts 48 may be placed horizontal or inclined toward the back end of the plunger operation member 40. When the plunger operation member 40 is pressed, the lock parts 48 are reversed (elastically deformed) as indicated by the arrows, to cause sliding resistance. Hence, by pushing the plunger P, the lock parts 48 are locked to the back end 10e of the syringe 10 in a state of being able to climb over the back end 10e, as with the lock parts 47.

FIGS. 7 to 11 illustrate a collunarium ejector 3 which is a third embodiment of the disclosed quantitative syringe-type ejector. In the following description, the substantially same parts as those in the other embodiments are given the same reference signs and their description is omitted.

Figure 7:
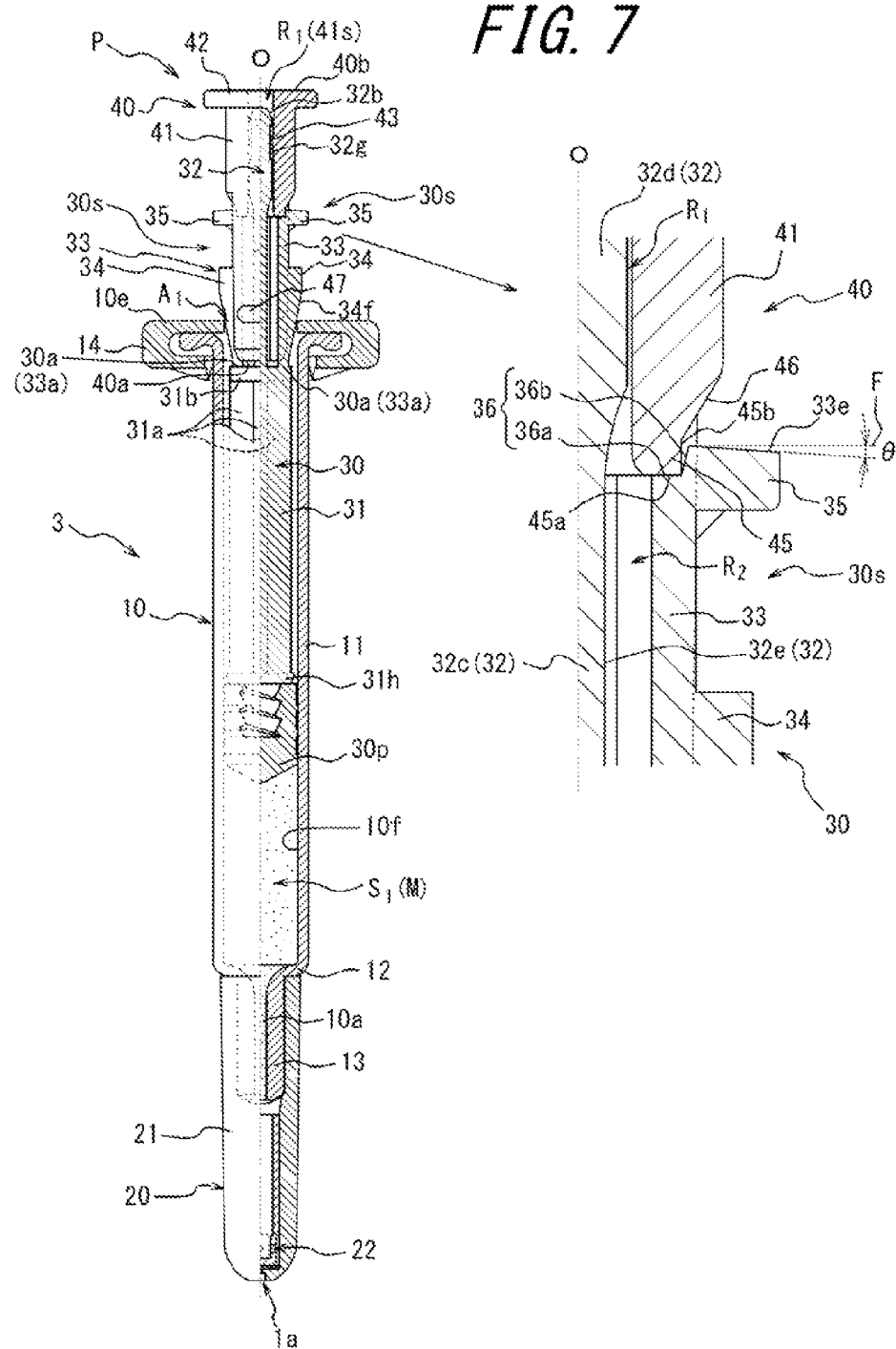
FIG. 7 is a side view illustrating a partial section of a collunarium ejector which is a third embodiment of the disclosed quantitative syringe-type ejector in an initial state before pushing a plunger operation member, and a partially enlarged view thereof.

As illustrated in FIG. 7, in the collunarium ejector 3 in this embodiment, the plunger P includes the piston holding member 30 and the plunger operation member 40.

Figure 8:
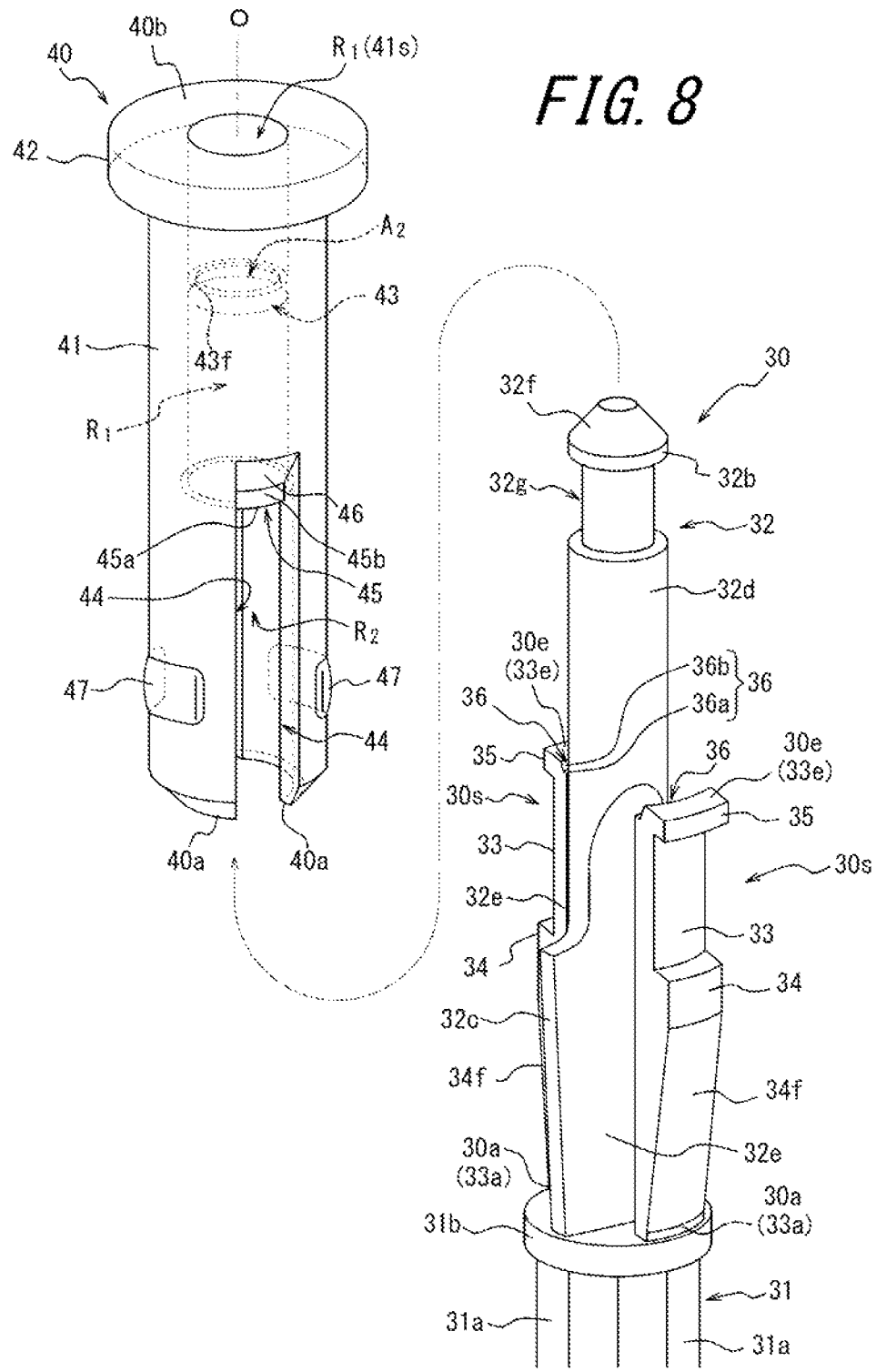
FIG. 8 is an exploded perspective view schematically illustrating a part of a piston holding member and the plunger operation member which are chief components of a plunger according to the third embodiment.

In the piston holding member 30, the shaft 32 includes a larger diameter part 32c connected to the disc part 31b and smaller in diameter than the disc part 31b, and a smaller diameter part 32d smaller in diameter than the larger diameter part 32c, as illustrated in FIG. 8. In this embodiment, the shaft 32 has a flat depression surface 32e as a result of forming a depression from the larger diameter part 32c to a portion of the smaller diameter part 32d, on each of opposite sides of the axis O. The smaller diameter part 32d has an annular groove 32g around the axis O, on its back end side. With the annular groove 32g being formed in the smaller diameter part 32d, the head 32b is formed at the back end of the shaft 32.

Each arm 33 is positioned facing the depression surface 32e formed in the shaft 32. The arm 33 can be displaced inward in the radial direction and returned to the initial position before the displacement, with the fixed end 33a as the origin.

In the plunger operation member 40, the opening $A_2$ formed on the inner side of the body 41 forms an inner diameter that is larger than the outer diameter of the annular groove 32g of the shaft 32 of the piston holding member 30 and smaller than the head 32b, as illustrated in FIG. 8. The annular projection 43 has the annular groove 32g portion of the shaft 32 pass through, and holds the head 32b so as not to slip off, as illustrated in the enlarged view in FIG. 9.

In this embodiment, the abutting end 45 of each notch 44 is formed as a projection having an equal thickness as its abutting side surface 45b extends backward along the axis O, as illustrated in the enlarged view in FIG. 7. Further, the abutting end 45 leads to the outer surface of the body 41 via an inclined surface 46 that is inclined outward in the radial direction toward the back, as illustrated in the enlarged view in FIG. 7.

Figure 9:
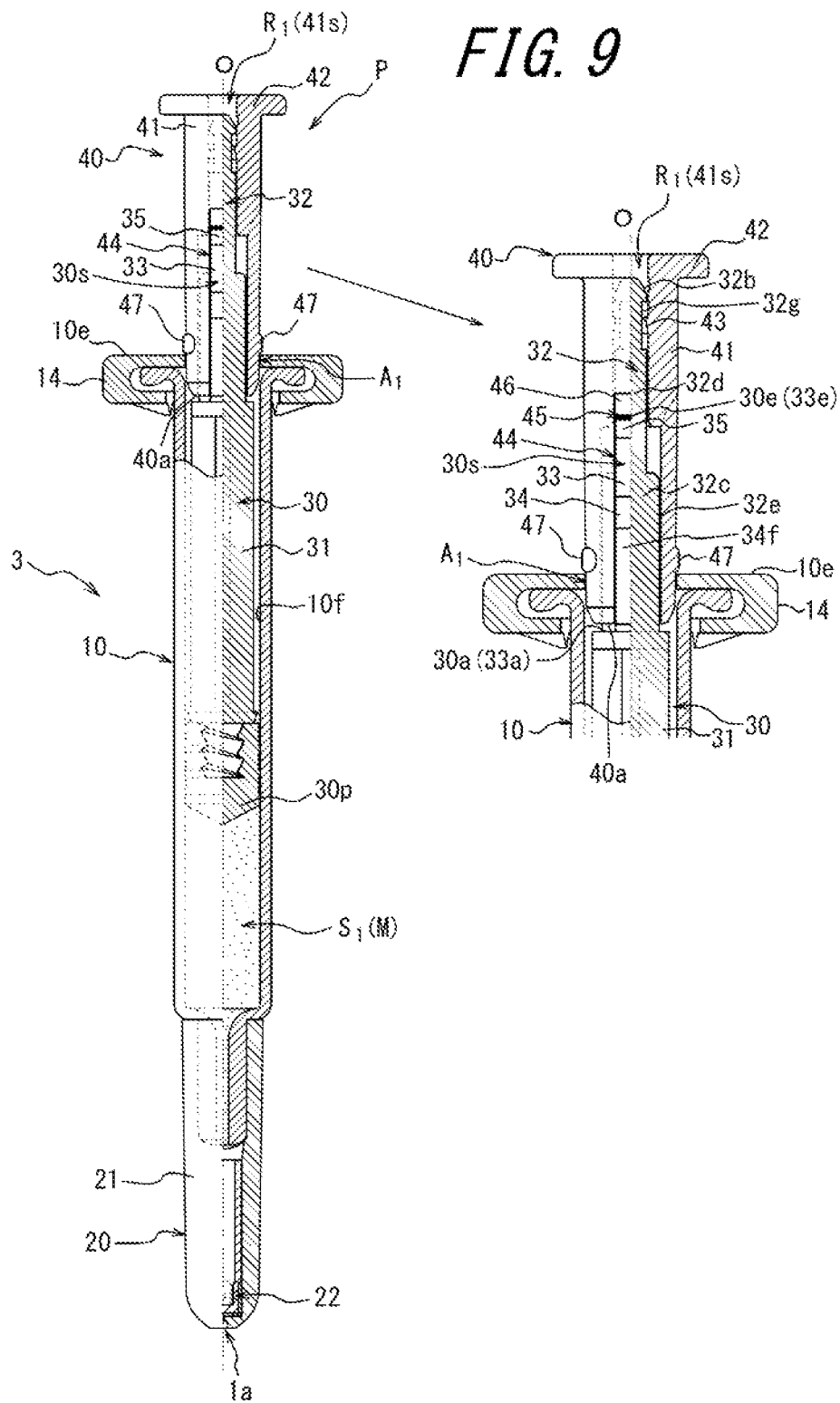
FIG. 9 is another side view illustrating a partial section of the collunarium ejector in the initial state illustrated in FIG. 7, and a partially enlarged view thereof.

The body 41 of the plunger operation member 40 is also provided integrally with one lock part 47 on each of opposite sides of the axis O, as illustrated in FIG. 9. The lock parts 47 are provided at two positions between the notches 44, and provided at the same position in the direction of the axis O as the inclined surface 34f of the slide projection 34 on the front end 40a side of the body 41 of the plunger operation member 40.

Figure 10A:
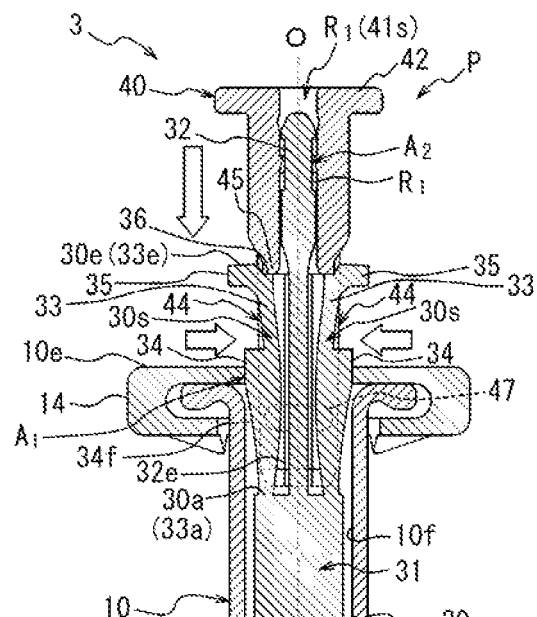
FIG. 10A is an enlarged sectional view illustrating the collunarium ejector in a state when the plunger operation member has been pushed to start the first ejection according to the third embodiment.
Figure 10B:
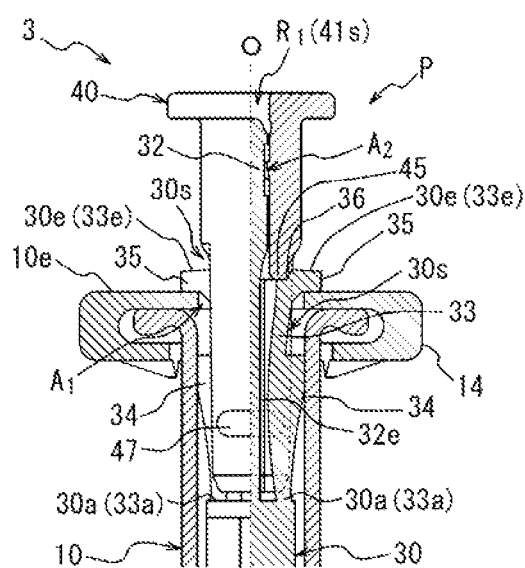
FIG. 10B is an enlarged sectional view illustrating the collunarium ejector in a state when the first ejection illustrated in FIG. 10A has ended.
Figure 10C:
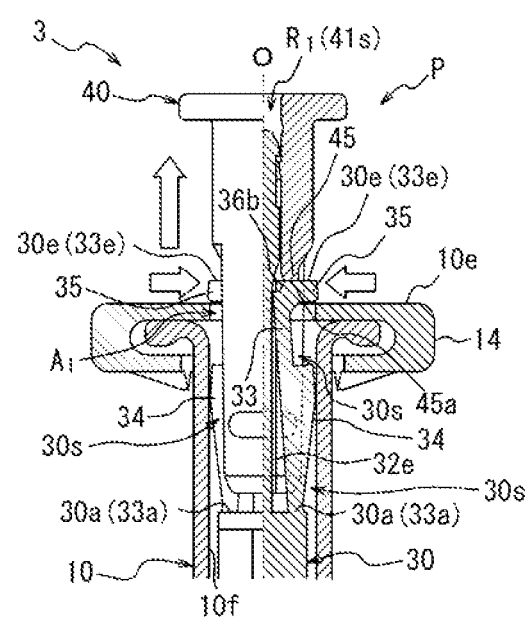
FIG. 10C is an enlarged sectional view illustrating the collunarium ejector in a state when, after the end state illustrated in FIG. 10B, the push of the plunger operation member has been released to start the second ejection.

In this embodiment, when the piston holding member 30 is pushed by the plunger operation member 40 so that the slide projections 34 of the piston holding member 30 enter into the syringe 10 from the back end opening $A_1$ of the syringe 10, each arm 33 is flexure-deformed with the slide projection 34 as the origin, as illustrated in FIGS. 10A and 10B. When the push is released, the free end 33e side of the arm 33 is deformed (restored) diagonally inward with the slide projection 34 as the origin, as illustrated in FIG. 10C. This is because, even though the whole arm 33 tries to return to the original shape, the fixed end 33a side of the arm 33 remains deformed inward with the slide projection 34 as the origin.

In this embodiment, even after the push of the plunger operation member 40 is released and the free end 33e side of each arm 33 is deformed diagonally inward (restored), the lock projections 35 of the piston holding member 30 are caught in contact with the back end 10e of the syringe 10, thus restricting the push of the syringe operation member 40, i.e. the further entrance of the piston holding member 30 into the syringe 10, as illustrated in FIG. 10C.

In this embodiment, the lock between the lock projections 35 of the piston holding member 30 and the back end 10e of the syringe 10 can be released when the abutting ends 45 of the plunger operation member 40 press the lock projections 35 with at least a predetermined force. In this embodiment, the size of projection (the amount of contact with the back end 10e of the syringe 10) of each lock projection 35 of the piston holding member 30 from the radially outer surface of the arm 33 is adjusted to enable the lock to be released with the predetermined force. The amount of contact of each lock projection 35 with the back end 10e of the syringe 10 in the state in FIG. 10C is set to be equal to the pressing force for releasing the lock between each lock part 47 and the back end 10e of the syringe 10 in FIG. 9. In other words, the first ejection and the second ejection are enabled using the same pressing force. Note that the predetermined force necessary to release the lock may be set as appropriate depending on the user, the contents, the purpose of use, etc.

The method of using the collunarium ejector 3 is described below.

First, the user pushes the plunger operation member 40 of the collunarium ejector 3 in the state illustrated in FIG. 7.

In this embodiment, since the abutting end surface 45a of the plunger operation member 40 is formed at the abutting end 45 leading to the inclined surface 46 of the body 41 and the abutting end 45 is housed in the level difference 36 of the arm 33 as illustrated in the enlarged view in FIG. 7, the level difference side surface 36b of the arm 33 functions as a regulation part for regulating the inward displacement of the arm 33.

In this embodiment, when the piston holding member 30 is pushed into the syringe 10, for example, the slide projection 34 of each arm 33 is pressed inward by the inner peripheral surface of the back end 10e of the syringe 10 defining the back end opening $A_1$ of the syringe 10, as illustrated in FIG. 10A. During this, the movement of the fixed end 33a side of the arm 33 is restrained by the syringe 10. While the arm 33 provided in the piston holding member 30 is flexure-deformed between the fixed end 33a and free end 33e of the arm 33 with the slide projection 34 as the origin as illustrated in FIG. 10A, the slide projection 34 slides along the inner peripheral surface 10f of the syringe 10, thus allowing the plunger operation member 40 to be pushed.

After the lock between each lock part 47 of the plunger operation member 40 and the back end 10e of the syringe 10 is released in this way, the contents M can be ejected in fixed amount from the ejection opening 1a into the nostril until each lock projection 35 provided on the arm 33 of the piston holding member 30 is caught by and locked to the back end 10e of the syringe 10 as illustrated in FIG. 10B. In this embodiment, the two depression surfaces 32e are formed in the shaft 32 of the piston holding member 30, and the respective arms 33 are set facing the depression surfaces 32e. Accordingly, even when each arm 33 is flexure-deformed, the arm 33 is kept from interfering with the shaft 32. A large amount of flexure when the arm 33 is flexure-deformed can thus be secured without increasing the radial dimension of the plunger operation member 40.

When the lock projections 35 of the piston holding member 30 are caught by and locked to the back end 10e of the syringe 10, the plunger operation member 40 can no longer be pushed into the syringe 10. The lock projections 35 of the piston holding member 30 thus function as a stopper by being locked to the back end 10e of the syringe 10. The first ejection ends here, with the contents M being left in the packing space $S_1$. The content of the packing space $S_1$ at this point may be selected as appropriate depending on the purpose of use. For example, the content is half the volume of the packing space $S_1$ before the ejection starts.

After this, when the push of the plunger operation member 40 is released, with the force of restoration of each arm 33 of the piston holding member 30 from the flexure deformation, only the free end 33e side of the arm 33 is deformed (restored) with the slide projection 34 as the origin, as illustrated in FIG. 10C. In this embodiment, when the free end 33e side of the arm 33 is deformed inward (restored) with the slide projection 34 as the origin, the abutting end 45 of the plunger operation member 40 is guided to the level difference side surface 36b of the arm 33, as illustrated in FIG. 10C. In this case, the free end 33e side of the arm 33 is released from the regulation by the plunger operation member 40 while pushing the plunger operation member 40 back, and so can be easily restored inward, as illustrated in FIG. 10C.

In this embodiment, however, even after the arm 33 of the piston holding member 30 is deformed diagonally inward with the slide projection 34 as the origin, the lock between the lock projection 35 of the arm 33 and the back end 10e of the syringe 10 is maintained, as illustrated in FIG. 10C. Hence, upon the second ejection, too, the plunger operation member 40 needs to be pushed with the pressing force for releasing the lock between the lock projection 35 of the arm 33 and the back end 10e of the syringe 10. In other words, upon the second ejection, too, the plunger operation member 40 cannot be pushed together with the piston holding member 30 until the force of pushing the plunger operation member 40 reaches the predetermined force or more.

Figure 11:
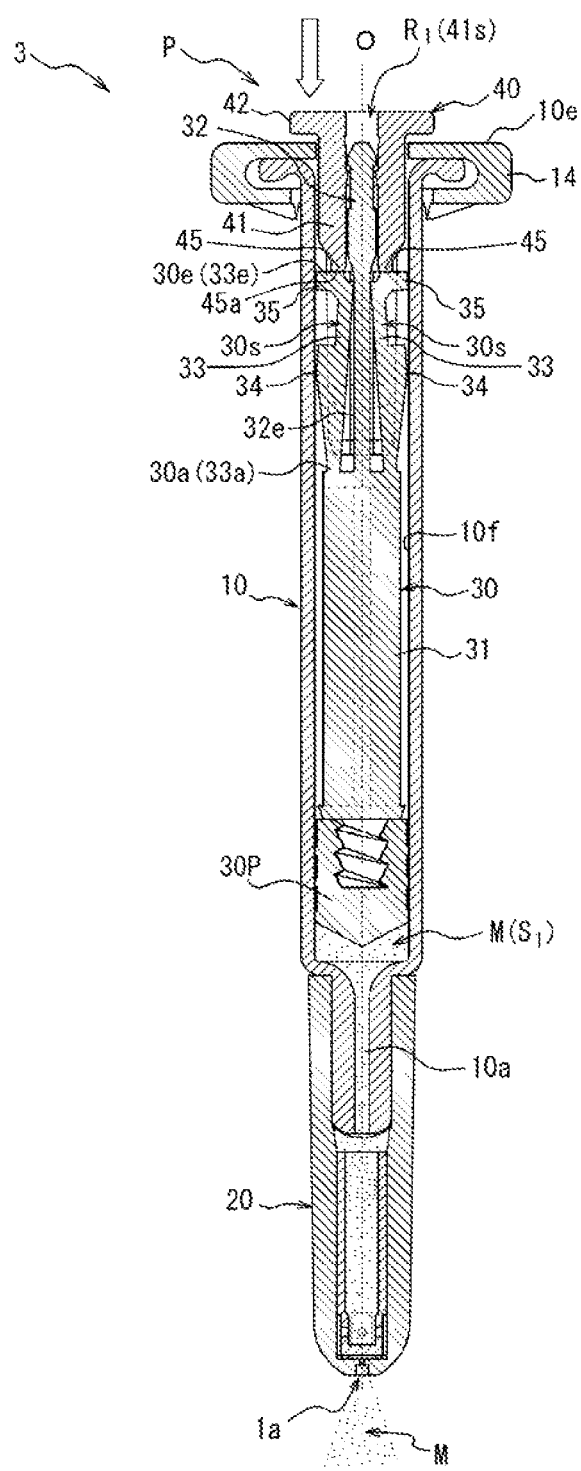
FIG. 11 is a sectional view illustrating the collunarium ejector in a state when the second ejection has been performed according to the third embodiment.

When the user further pushes the plunger operation member 40 with a strong force, the lock between the lock projection 35 of the arm 33 of the piston holding member 30 and the back end 10e of the syringe 10 is released, as a result of which the plunger operation member 40 can be swiftly pushed together with the piston holding member 30 with a strong force, as illustrated in FIG. 11. Pushing the plunger operation member 40 in this way releases the lock between the lock projection 35 of the arm 33 and the back end 10e of the syringe 10. At this moment, the piston holding member 30 swiftly and forcefully pushes out the contents M in the syringe 10 from the through hole 10a, as in the first ejection. As a result of being swiftly and forcefully pushed out from the through hole 10a of the syringe 10, the contents M can be stably ejected from the ejection opening 1a formed in the nozzle 20 while maintaining a constant state.

Thus, in this embodiment, after the push of the plunger operation member 40 is released as illustrated in FIG. 10C, the nozzle 20 is inserted into the other nostril and the plunger operation member 40 is pushed again, as a result of which the contents M remaining in the packing space $S_1$ can be stably ejected from the ejection opening 1a while maintaining a constant state in the second ejection as in the first ejection, as illustrated in FIG. 11. Even when each arm 33 is deformed diagonally inward with the slide projection 34 as the origin, the arm 33 is kept from interfering with the shaft 32 because the depression surface 32 is formed in the shaft 32. A large amount of flexure when the arm 33 is flexure-deformed diagonally inward with the slide projection 34 as the origin can thus be secured without increasing the radial dimension of the plunger operation member 40.

As described above, according to this embodiment, the contents M packed in one syringe 10 can be stably ejected in small quantities while maintaining a constant state. Moreover, in this embodiment, releasing the push of the plunger operation member 40 and then pushing the plunger operation member again enables the second ejection. The user does not need to switch the collunarium ejector 3 from one hand to the other upon the second ejection. The user can therefore expel the contents M in small quantities with one hand.

In this embodiment, the plunger operation member 40 has the lock parts 47 that are releasably locked to the back end 10e of the syringe 10, where the lock projections 35 of the piston holding member 30 are located behind the lock parts 47 when the plunger operation member 40 is mounted on the piston holding member 30, as illustrated in FIG. 9. In this case, since the lock parts 47 of the plunger operation member 40 are caught by the back end 10e of the syringe 10 even before the user starts pushing the plunger operation member 40, the first ejection can be stably performed while maintaining the constant state.

In this embodiment, the level difference 36 pushed by the plunger operation member 40 is provided on the inner side of the free end 33e of each arm 33 as illustrated in the enlarged view in FIG. 7, so that the push from the plunger operation member 40 can be efficiently transferred to the piston holding member 30. The same applies to the case where the plunger operation member 40 is provided with each extension rib (projection) 45c on the inner side of the abutting end 45 as a pressing part for pushing the free end 33e of the arm 33 as in the below-mentioned fourth embodiment.

Figure 12A:
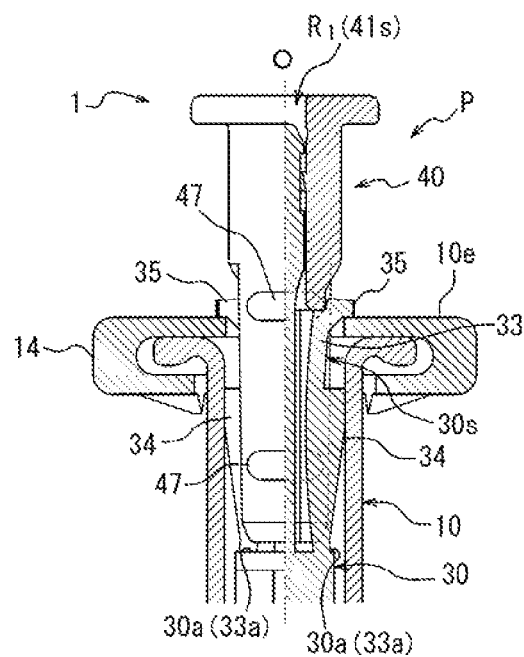
FIG. 12A is an enlarged sectional view illustrating a partial side of the collunarium ejector in a state when the plunger operation member illustrated in FIG. 3A has been pushed and the first ejection has ended.

In the foregoing first embodiment, the plurality of lock parts 47 are arranged at an interval along the axis O in the plunger operation member 40 in order to stably perform the second ejection, as illustrated in FIG. 12A as an example.

However, the plunger operation member 40 is mounted on the piston holding member 30 with the clearance space 41s being formed in the direction of the axis O, in order to ensure the second ejection operation. When each arm 33 of the piston holding member 30 is deformed diagonally inward (restored) with the slide projection 34 as the origin, the plunger operation member 40 is pushed back along the direction of the axis O. In the case where the two lock parts 47 are provided on the plunger operation member 40, when each arm 33 of the piston holding member 30 is deformed diagonally inward (restored) with the slide projection 34 as the origin after the first ejection operation ends, the lock part 47 provided on the plunger operation member 40 is pushed back along the direction of the axis O by play Δx, as illustrated in FIG. 12B.

Thus, in the case where the plurality of lock parts 47 are provided on the plunger operation member 40 to be caught by the back end 10e of the syringe 10, there is a possibility that the lock part 47 of the plunger operation member 40 deviates backward along the direction of the axis O from the back end 10e of the syringe 10. Such deviation enables a fine ejection operation by pushing by the deviation (play Δx), between the first ejection operation and the second ejection operation. As a result of this fine ejection operation, the initial operation in the second ejection operation can be performed with a light force. In other words, the force of the initial operation can be used to release the lock state between the lock part 47 and the back end 10e of the syringe 10 in the second ejection operation.

Figure 12B:
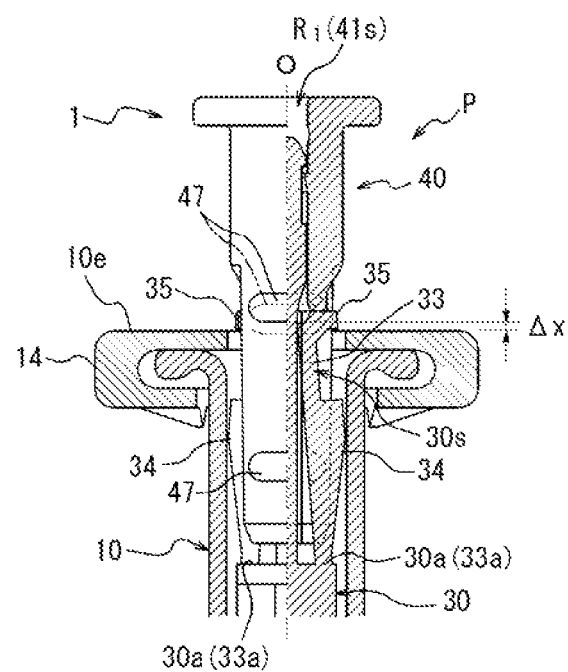
FIG. 12B is an enlarged sectional view illustrating a partial side of the collunarium ejector in a state immediately after the push of the plunger operation member has been released to start the second ejection after the end state illustrated in FIG. 12A.

Meanwhile, after the first ejection ends, the piston holding member 30 is held in the syringe 10 by the slide projection 34 of each arm 33 of the piston holding member 30 in both the first and third embodiments, as illustrated in FIGS. 12B and 10C. Accordingly, once each lock projection 35 of the piston holding member 30 is caught by the back end 10e of the syringe 10 as in the third embodiment, the lock projection 35 will not deviate from the back end 10e of the syringe 10 as illustrated in FIG. 10C. Thus, in this embodiment, more accurate quantitative ejection is achieved by preventing fine ejection between the first ejection operation and the second ejection operation.

Figure 13A:
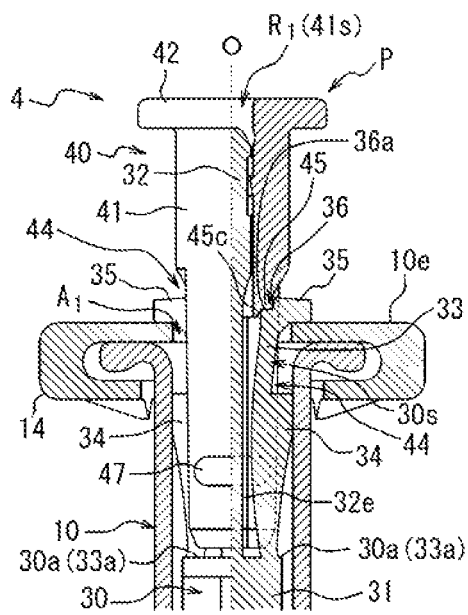
FIG. 13A is an enlarged view illustrating a partial side of a collunarium ejector which is a fourth embodiment of the disclosed quantitative syringe-type ejector in a state when the first ejection has ended.
Figure 13B:
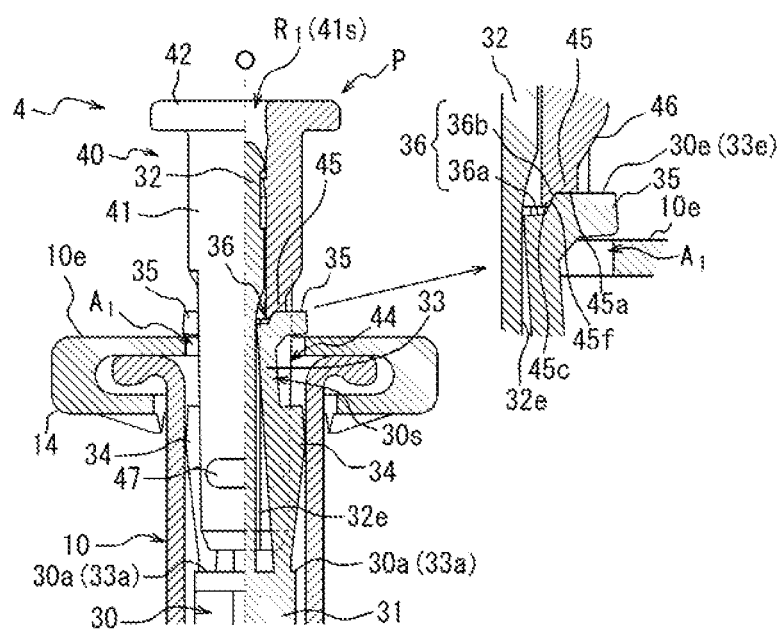
FIG. 13B is an enlarged sectional view illustrating a partial side of the collunarium ejector in a state immediately after the push of the plunger operation member has started to start the second ejection after the end state illustrated in FIG. 13A, and a more enlarged view thereof.

FIGS. 13A and 13B illustrate a collunarium ejector 4 which is a fourth embodiment of the disclosed quantitative syringe-type ejector. FIG. 13A illustrates a state when the first ejection has ended, and FIG. 13B illustrates a state immediately after the push of the plunger operation member 40 has started to start the second ejection. In this embodiment, the substantially same parts as those in the other embodiments are given the same reference signs and their description is omitted.

In the collunarium ejector 4 in this embodiment, the abutting ends 45 provided in the plunger operation member 40 have been changed in shape. In this embodiment, an extension rib 45c is provided on the inner side of each abutting end 45, as illustrated in the enlarged view in FIG. 13B. The extension rib 45c has an inclined surface 45f inclined so that the extension rib 45c is tapered toward its tip.

For example, in the first ejection, the inclined surface 45f of the extension rib 45c is in contact with the inner surface of the arm 33 of the piston holding member 30 leading to the level difference 36 of the arm 33 as illustrated in FIG. 13A, to restrict the radially inward deformation of the lock projection 35 of the arm 33 up to a predetermined position. Immediately after the plunger operation member 40 is further pushed to start the second ejection, the inclined surface 45f of the extension rib 45c is in contact with the level difference side surface 36b of the piston holding member 30 as illustrated in the enlarged view in FIG. 13B, to restrict the radially inward deformation of the lock projection 35 of the arm 33 up to a predetermined position.

In this embodiment, by restricting the deformation of the free end 33e side of the arm 33 in the above-mentioned manner, the end of the first ejection is ensured, and also it is ensured upon the second ejection that the inward displacement of the free end 33e of the arm 33 is suppressed in the lock state between the lock projection 35 of the arm of the piston holding member 30 and the back end 10e of the syringe 10. Since a greater pressing force is required to release this lock state, the contents M can be swiftly and forcefully pushed out more reliably.

Figure 14A:
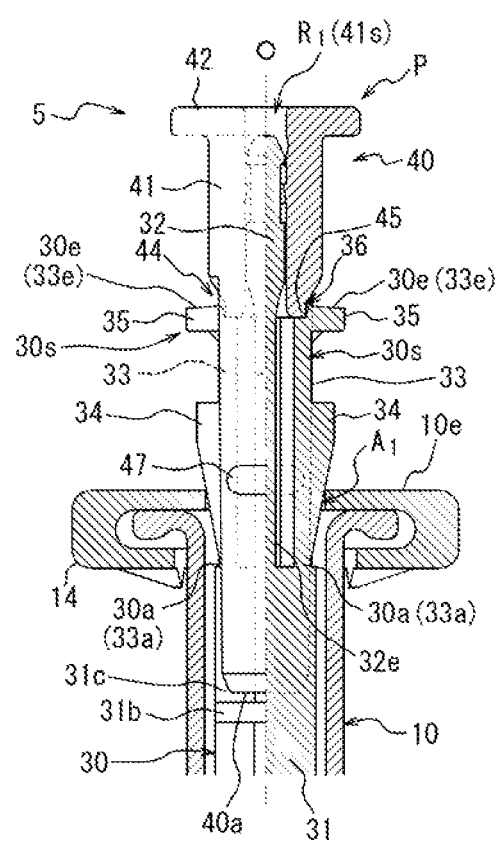
FIG. 14A is an enlarged sectional view illustrating a partial side of a collunarium ejector which is a fifth embodiment of the disclosed quantitative syringe-type ejector in an initial state before pushing a plunger operation member, as seen from a lock part provided on the plunger operation member.
Figure 14B:
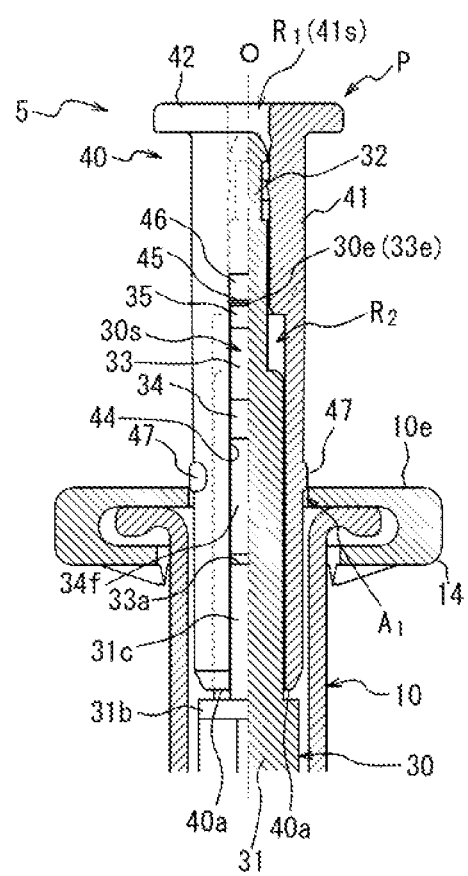
FIG. 14B is an enlarged sectional view illustrating a partial side of the collunarium ejector illustrated in FIG. 14A, as seen from a notch (an arm of a piston holding member) formed in the plunger operation member.

FIGS. 14A and 14B illustrate a collunarium ejector 5 which is a fifth embodiment of the disclosed quantitative syringe-type ejector. FIGS. 14A and 14B illustrate the collunarium ejector 5 in the initial state before pushing the plunger operation member 40, from different directions. In this embodiment, the substantially same parts as those in the other embodiments are given the same reference signs and their description is omitted.

In the collunarium ejector 5 in this embodiment, the front end 40a of the plunger operation member 40 extends forward more than those in the third and fourth embodiments. For example, in FIG. 14A, when the plunger operation member 40 is mounted on the piston holding member 30, the front end 40a of the plunger operation member 40 extends ahead of the fixed end 33a of each arm 33 provided on the piston holding member 30. In this embodiment, the piston holding member 30 has a raised part 31c on the disc part 31b of the body 31, and connects the fixed end 33a of the arm 33 to the raised part 31c.

In this embodiment, by extending the front end 40a of the plunger operation member 40, the tilt (wobbling) of the plunger operation member 40 when mounted on the piston holding member 30 is suppressed. Hence, the piston holding member 30 and the plunger operation member 40 can be assembled together in a stable state.

Here, by using the abutting end 45 of the plunger operation member 40 as a pressing part for pushing the arm 33 of the piston holding member 30 as in each of the foregoing embodiments, the arm 33 can be pushed by the plunger operation member 40 without using another member.

Note that, while the abutting end 45 of the plunger operation member 40 presses the level difference 37 of the arm 33, the front end 40a may press the disc part 31b simultaneously.

Various changes may be made to the embodiments described above. For example, the lock parts 47 (48) may be provided only at the same position as the lock projections 35 in the direction of the axis O. Thus, the lock parts 47 (48) may be provided at one or more positions in the direction of the axis O. Moreover, the number of arms 33 and the number of notches 44 may be 3 or more. In particular, evenly-spaced arrangement as in the embodiments stabilizes the balance around the axis, with it being possible to realize favorable operation. Although the foregoing embodiments describe the case where the quantitative syringe-type ejector is a spray ejector, the contents may be ejected in various forms such as foam and normal liquid. The structures of the embodiments described above may be replaced or combined with each other as appropriate.

INDUSTRIAL APPLICABILITY

The disclosed quantitative syringe-type ejector may be applied to any of various structures including a syringe and a plunger pushable into the syringe. Moreover, various contents not limited to collunarium may be used.

REFERENCE SIGNS LIST 1 collunarium ejector (first embodiment)
1a ejection opening 3 collunarium ejector (third embodiment)
4 collunarium ejector (fourth embodiment)
5 collunarium ejector (fifth embodiment)
10 syringe
10e back end of syringe
10f inner peripheral surface of syringe
20 nozzle (spray nozzle)
30 piston holding member
30p piston
30s stopper
30a fixed end of stopper
30e free end of stopper
31 body
32 shaft
32a shaft body
32b head (slip-off prevention part)
32c larger diameter part
32d smaller diameter part
32e depression surface
32g annular groove
33 arm
33a fixed end of arm
33e free end of arm
34 slide projection
35 lock projection
36 level difference
36a level difference bottom surface (pressed surface)
36b level difference side surface (pressed surface)
40 plunger operation member
40a front end
40b back end
41 body
41s clearance space
43 annular projection (slip-off prevention part)
44 notch
45 abutting end (pressing part)
45a abutting end surface (pressing surface)
45b abutting side surface (tapered surface)
45c extension rib (projection)
45f inclined surface
47 lock part
48 lock part
$A_1$ back end opening of syringe
M contents
P plunger
$R_1$ internal surface
$R_2$ internal surface
$S_1$ packing surface

The invention claimed is:

1. A quantitative syringe-type ejector comprising:
a syringe; and
a plunger pushable into the syringe,
wherein:
the plunger includes: a piston holding member having a piston in front and at least one arm extending backward; and a plunger operation member located behind the piston holding member to press the at least one arm forward;
the piston holding member has, on each of the at least one arm: a slide projection for deforming each arm inward while sliding on an inner peripheral surface of the syringe; and a lock projection located behind the slide projection to be locked to a back end of the syringe,
the lock projection of each of the at least one arm is configured so that a locked state of each lock projection to the back end of the syringe is released when the plunger operation member is pushed in a state where the at least one arm is deformed inward,
the plunger operation member has at least one lock part to be releasably locked to the back end of the syringe, and
a level difference for being pressed by the plunger operation member is provided on an inner side of a back end of the at least one arm.

2. The quantitative syringe-type ejector according to claim 1, wherein the lock projection of each of the at least one arm is located behind at least one of the at least one lock part.

3. The quantitative syringe-type ejector according to claim 1, wherein the at least one lock part includes a plurality of lock parts arranged at an interval in an axial direction, and at least one of the plurality of lock parts is located ahead of the lock projection of each of the at least one arm.

4. The quantitative syringe-type ejector according to claim 1, wherein the lock projection of each of the at least one arm is locked so that the locked state is released when pressed by the plunger operation member.

5. The quantitative syringe-type ejector according to claim 1, wherein a side surface of the level difference is a tapered surface.

6. The quantitative syringe-type ejector according to claim 1, wherein the plunger operation member has a projection on an inner side of a pressing part for pressing the at least one arm.

7. The quantitative syringe-type ejector according to claim 1, wherein the plunger operation member has a notch for operably housing each of the at least one arm, and an abutting end provided on the plunger operation member defining the notch is a pressing part for pressing the at least one arm.

8. The quantitative syringe-type ejector according to claim 7, wherein the abutting end of the plunger operation member has a tapered surface.

9. The quantitative syringe-type ejector according to claim 1, further comprising a slip-off prevention part for holding the piston holding member and the plunger operation member so as not to slip off each other, while enabling the plunger operation member to be pushed back by inward deforming of the at least one arm.

10. The quantitative syringe-type ejector according to claim 1, wherein each of the at least one lock part is a protuberance protruding from the plunger operation member.

11. The quantitative syringe-type ejector according to claim 1, wherein each of the at least one lock part is an elastically deformable reverse part projecting from the plunger operation member.

12. The quantitative syringe-type ejector according to claim 1, wherein a spray nozzle is provided at a front end of the syringe.

* * * * *